United States Patent
Hart et al.

(10) Patent No.: US 10,130,390 B1
(45) Date of Patent: Nov. 20, 2018

(54) SYSTEM FOR ABRADING SKIN TO REMOVE OUTER PORTIONS THEREOF

(71) Applicants: Jackie Hart, Rocklin, CA (US); Leonard Hofheins, Provo, UT (US)

(72) Inventors: Jackie Hart, Rocklin, CA (US); Leonard Hofheins, Provo, UT (US)

(73) Assignee: Dermasweep, Inc., Rocklin, CA (US)

( * ) Notice: Subject to any disclaimer, the term of this patent is extended or adjusted under 35 U.S.C. 154(b) by 290 days.

(21) Appl. No.: 15/051,328

(22) Filed: Feb. 23, 2016

Related U.S. Application Data

(62) Division of application No. 11/172,698, filed on Jun. 30, 2005, now abandoned.

(51) Int. Cl.
*A61B 17/54* (2006.01)
*A61B 17/32* (2006.01)

(52) U.S. Cl.
CPC .. *A61B 17/54* (2013.01); *A61B 2017/320012* (2013.01)

(58) Field of Classification Search
CPC ........... A61B 2017/00761; A61B 2017/00747; A61B 2017/00752; A61B 2017/00756; A61B 17/54; A61B 2017/320012
See application file for complete search history.

(56) References Cited

U.S. PATENT DOCUMENTS

| | | |
|---|---|---|
| 2,701,559 A | 2/1955 | Cooper |
| 2,712,823 A | 7/1955 | Kurtin |
| 2,867,214 A | 1/1959 | Wilson |
| 2,881,763 A | 4/1959 | Robbins |
| 2,921,585 A | 1/1960 | Schumann |
| 3,964,212 A | 6/1976 | Karden |
| 4,378,804 A | 4/1983 | Cortese, Jr. |
| 4,646,482 A | 3/1987 | Chitjian |
| 4,957,747 A | 9/1990 | Stiefel |
| 5,012,797 A | 5/1991 | Liang et al. |
| 5,035,089 A | 7/1991 | Tillman et al. |
| 5,037,431 A | 8/1991 | Summers et al. |
| 5,037,432 A | 8/1991 | Molinari |
| 5,100,412 A | 3/1992 | Rosso |
| 5,121,388 A | 6/1992 | Perdikaris et al. |
| 5,207,234 A | 5/1993 | Rosso |
| 5,800,446 A | 9/1998 | Banucri |
| 5,810,842 A | 9/1998 | Di Fiore et al. |
| 5,971,999 A | 10/1999 | Naldoni |
| 6,042,552 A | 3/2000 | Cornier |
| 6,241,739 B1 | 6/2001 | Waldron |
| 6,423,078 B1 | 7/2002 | Bays et al. |
| 6,500,183 B1 | 12/2002 | Waldron |
| 2004/0122447 A1 * | 6/2004 | Harmon ............. A61B 17/54 606/131 |

* cited by examiner

*Primary Examiner* — Tuan V Nguyen

(74) *Attorney, Agent, or Firm* — Thomas R. Lampe

(57) ABSTRACT

A system for abrading skin to remove outer portions thereof includes an apparatus having a skin abrading head with a head portion and a skin abrading brush. The outer head portion has a rim for placement in contact with the skin along with the bristles of the brush. Air flow is generated in the head to bring the skin into engagement with the rim and bristles and transport removed skin portions.

7 Claims, 8 Drawing Sheets

SYSTEM FOR ABRADING SKIN TO REMOVE OUTER PORTIONS THEREOF

This Application is a divisional patent application based on and claiming the benefit of U.S. patent application Ser. No. 11/172,698, filed Jun. 30, 2005, which is now abandoned.

TECHNICAL FIELD

This invention relates to apparatus for abrading skin to remove outer portions thereof as well as to a method. The system has particular application to microabrading skin by removing outer layers to provide a fresh skin surface.

BACKGROUND OF THE INVENTION

Dermabrasion, sometimes referred to as microdermabrasion, is a well known process for removing dead cells from the outermost layer of the skin, cleaning out blocked pores and enhancing skin tone. U.S. Pat. No. 6,241,739, discloses a treatment tool and tissue collection system for removing outer layers of skin to provide a revitalized, fresh skin surface, the objective being to remove dead end old cell skins without damaging the remaining skin surface and without the use of powdered abrasive material.

More particularly, U.S. Pat. No. 6,241,739 discloses a device for microabrasion comprising a hollow tube with an abrasive material permanently attached to a skin contacting end. The abrasive coated tip is moved over the skin surface while a vacuum is applied through the tube to the skin surface to remove The abrasive coated tip is moved over the skin surface while a vacuum is applied through the tube to the skin surface to remove cells abraded from the skin surface. The vacuum also causes the skin to be held in intimate contact with the abrasive tip during the treatment procedure. Specifically suggested as abrasion particles attached to the treatment tip are diamond grit, aluminum oxide, silicon carbide, silicon oxide, and various metal nitrates. Also suggested is the concept of machining or chemically treating the tip to provide a roughened surface which when moved across skin abrades the epidermis, dislodging cells from the surface. A method employing this technique is also disclosed in U.S. Pat. No. 6,241,739.

U.S. Pat. No. 6,500,183 matured from a continuation in-part application based on the patent application resulting in above-described U.S. Pat. No. 6,241,739. U.S. Pat. No. 6,500,183 discloses a treatment tool and tissue collection system for removal of outer layers of skin to provide a revitalized, fresh skin surface, and a method of using same. The tool is an abrasive tipped tool mounted on the end or within the end of a hollow tube, the tube being connected to a source of vacuum. The vacuum aids in maintaining intimate contact between the tip and the skin during the treatment process and transports the removed tissue to a collection container. The abrasive surface within the tube is a motor driven abrasive pad. Contact between the pad and the abrasive disc is brought about or increased by application of a vacuum through the tube to the skin surface. Other prior art abrasion techniques are known, some of which can be traced back to ancient times wherein alabaster and pumice were utilized to remove blemishes and rough spots and to make the skin smooth and soft.

U.S. Pat. Nos. 2,712,823, 2,867,214, 2,881,763 and 2,921,5,85 disclose abrasive tipped devices or rotating brushes and cylinders coated with abrasive particles such as diamond dust to remove skin layers.

U.S. Pat. No. 5,800,446 describes a stick, fingertip or glove palm coated with an abrasive material which is rubbed over the skin surface to provide a polishing action. U.S. Pat. No. 3,964,212 discloses a pneumatic grinding machine for flat surfaces. U.S. Pat. No. 4,378,804 discloses a skin abrasion device which uses flowing water to rotate an abrasive brush and create a vacuum to remove loosened skin particles. The rotating brush is usually employed in conjunction with a liquid detergent or medicinal compound applied to the skin surface being scrubbed.

U.S. Pat. No. 5,012,797 shows the use of an ultrasonic surgical tool adapted to abrase tissue wherein use of the tool is accompanied by use of rinsing liquid such as an aqueous saline solution and suction means to withdraw the rinsing fluid as well as blood and tissue fragments upwardly into a pipe for disposal. U.S. Pat. No. 5,037,431 describes a hand held surgical apparatus wherein a pressurized jet of a liquid, such as water or sterile saline, is employed to fragment diseased tissue and remove the liquid and fragmented tissue by vacuum.

It is also known to abrade the skin surface using powdered aluminum oxide or a liquid topical composition 10 containing suspended aluminum oxide, as disclosed for example in U.S. Pat. No. 4,957,747. In the arrangement of U.S. Pat. No. 5,037,432 abrasive reducing substances are conveyed under pressure to the skin and a collection tube removes under suction both the reducing substances and the portions of tissue removed during the treatment. Somewhat similar arrangements, employing collection chambers, are disclosed in U.S. Pat. Nos. 5,100,412, 5,207,234 and 5,810,842.

U.S. Pat. No. 5,971,999 is related to an apparatus for microdermabrading by means of a jet of a mixture of air and reducing crystals, and an associated handle. The jet of reducing crystals is, in particular, a jet of corundum crystals. U.S. Pat. No. 6,042,552 discloses a device for collecting fragments of walls of internal organs and U.S. Pat. No. 2,701,559 discloses apparatus for exfoliating and collecting diagnostic material from inner walls of hollow visera. U.S. Pat. Nos. 2,921,585, 5,207,234 and 6,423,078 show other dermabrasion approaches. U.S. Pat. Nos. 5,121,388, 4,646, 482 and 5,035,089 relate to non-medical abrasion systems.

DISCLOSURE OF INVENTION

The system of the present invention relates to a unique combination of structural elements which cooperate in a unique manner to abrade skin and remove the abraded skin. The invention is characterized by its high degree of effectiveness and ease of 10 use. The apparatus and method of the present invention are not taught or suggested by the known prior art, indicated above, whether taken alone or in combination.

The apparatus of the present invention incorporates apparatus for abrading skin to remove outer portions thereof including a hand-held member defining an air-flow passageway for communication with a vacuum source.

The apparatus further includes a skin abrading head connected to the hand-held member for engaging and abrading skin, the skin abrading head including a head portion having a rim for placement in contact with the skin. The head portion defines a head interior and an opening in communication with the head interior.

A skin abrading brush having a plurality of bristles is located in or adjacent to the head interior, the skin abrading brush is engageable with the skin when the rim is placed in contact therewith.

The skin abrading head defines at least one orifice providing communication between the air-flow passageway and the head interior for selectively pulling said skin in the direction of said rim and said skin abrading brush and for creating a vacuum induced air flow within the head interior entraining skin portions removed due to abrasion of the skin by the skin abrading brush and delivering. the skin portions to the air-flow passageway.

The method of the invention includes providing a hand held member defining a air-flow passageway connected to a skin abrading head including a head portion having a rim and a skin abrading brush having a plurality of bristles.

The rim and the bristles are substantially simultaneously brought into engagement with the skin.

While maintaining the engagement, the hand-held member is utilized to move the rim and the bristles along the skin.

During movement and while maintaining engagement, a vacuum is created in the air-flow passageway and in the head interior causing air flow from the ambient atmosphere through the head interior and past the bristles and into the air-flow passageway.

The vacuum is selectively employed to pull the skin in the direction of the rim and bristles and entrain portions of the skin abraded by the skin abrading brush in the air flow.

Other features, advantages and objects of the present invention will become apparent with reference to the following description and accompanying drawings.

MODES FOR CARRYING OUT THE INVENTION

Figure 1:
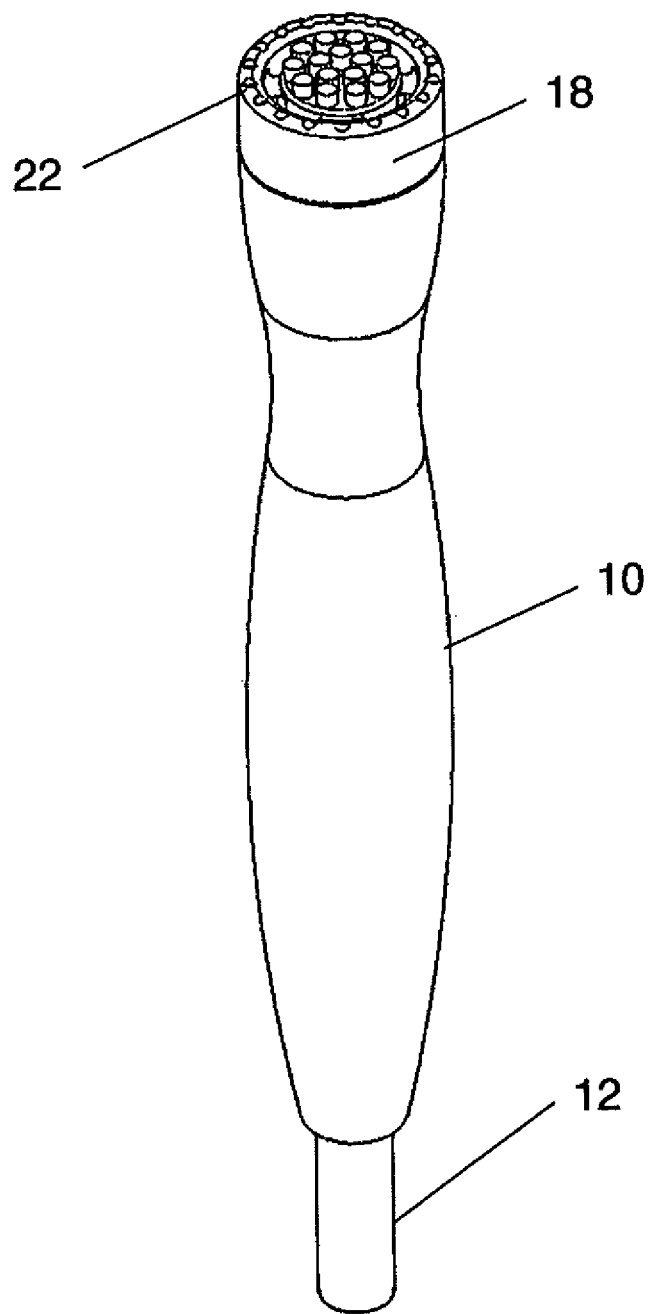
FIG. 1 is a perspective view of a preferred form of apparatus constructed in accordance with the teachings of the present invention.
Figure 2:
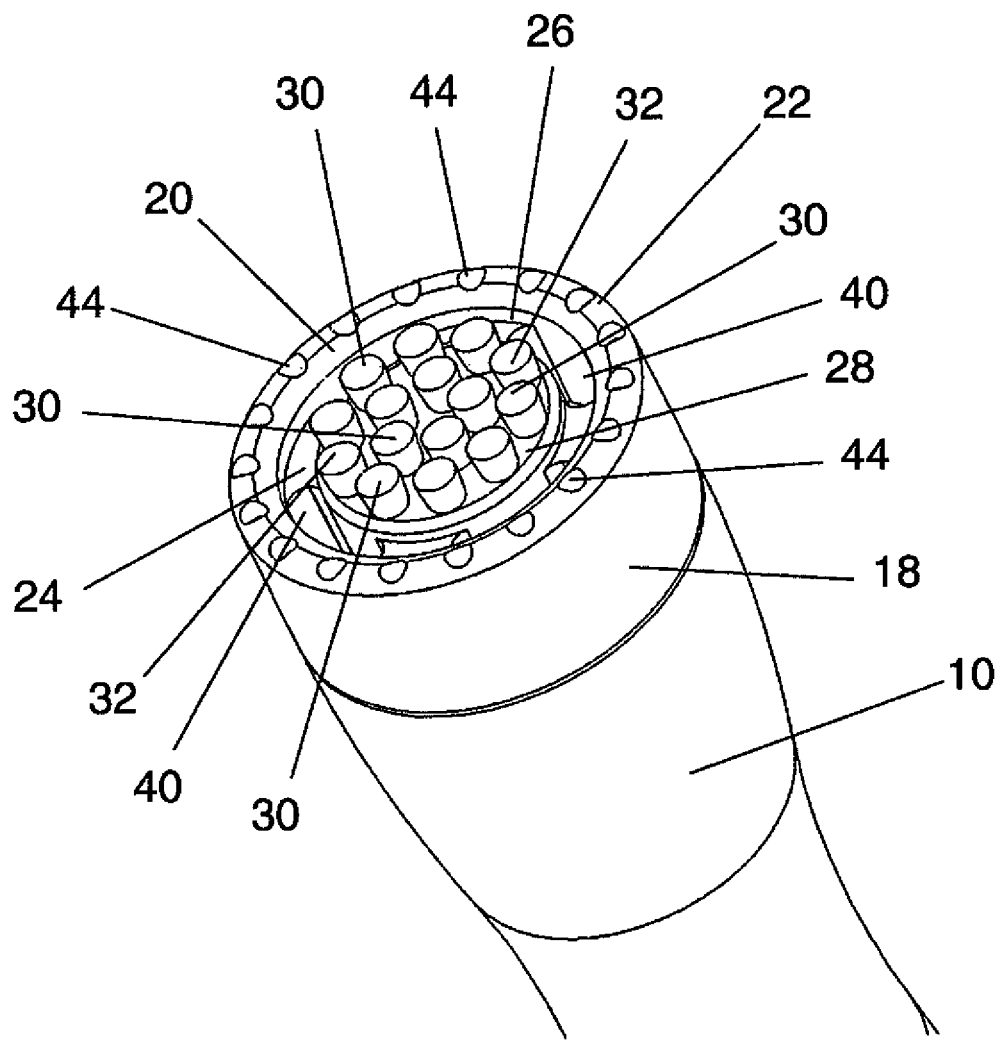
FIG. 2 is an enlarged, perspective view showing details of the skin abrading head incorporated in the apparatus.
Figure 3:
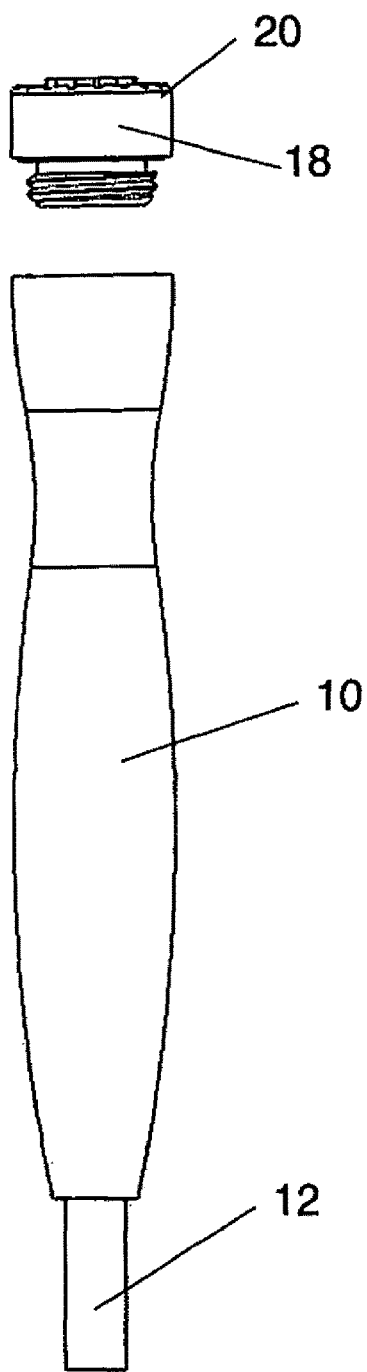
FIG. 3 is an exploded, elevational view showing the skin abrading head removed from the hand-held member of the apparatus.
Figure 4:
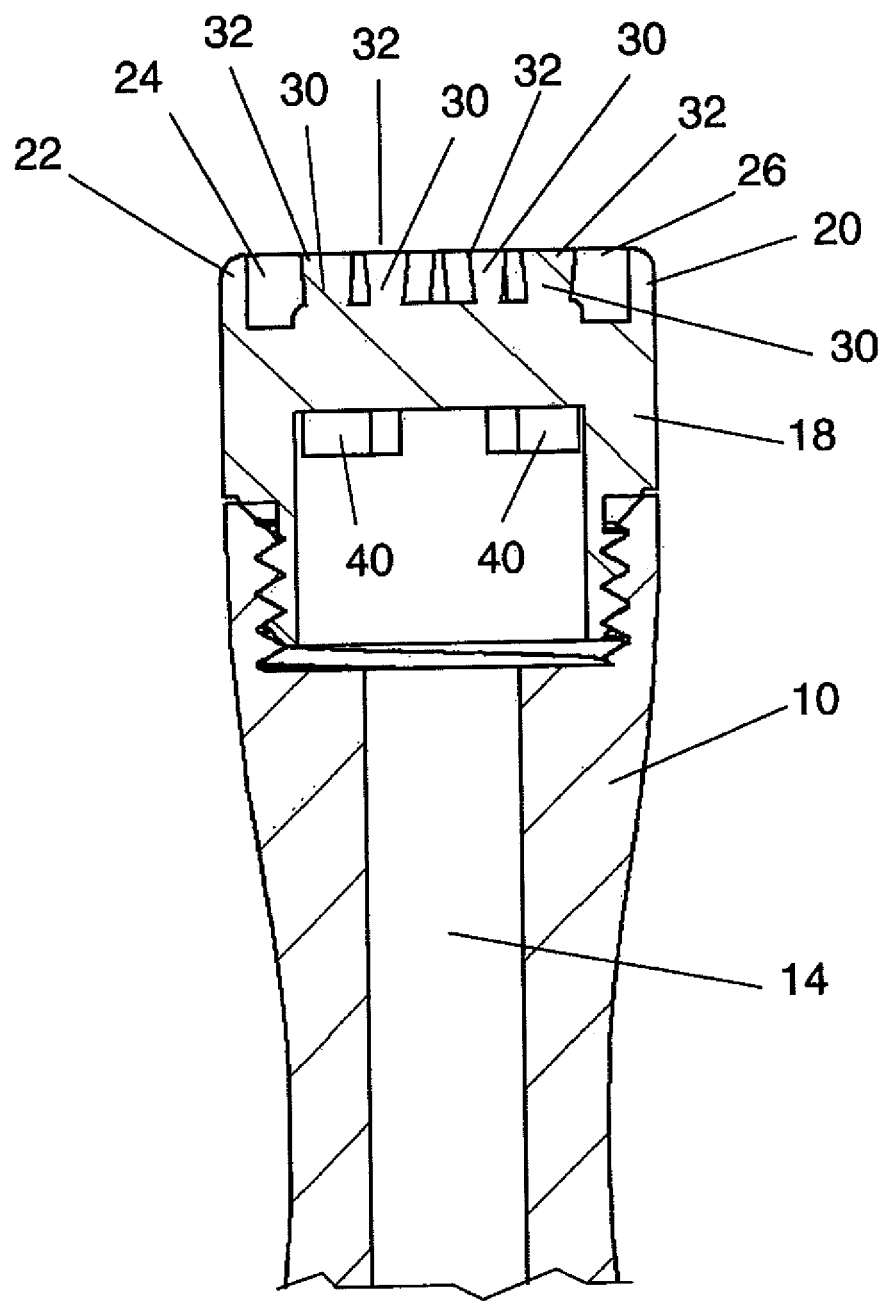
FIG. 4 is an enlarged, cross-sectional view showing the skin abrading head in operative association with a portion of the hand-held member.

FIGS. 1-4 illustrate a preferred embodiment of apparatus constructed in accordance with the teachings of the present invention. The apparatus is for abrading skin to remove outer portions thereof.

The apparatus includes a hand-held member 10 in the form of a handle and having a tube 12 extending from an end thereof. The tube 12 is for the purpose of connecting the hand held member to a suitable vacuum source (not shown). The hand held member 10 defines an air-flow passageway or lumen 14 for communication with the vacuum source through tube 12.

Threadedly engaged with the distal end of hand-held member 10 is a skin abrading head 18 utilized to engage and abrade skin of an individual. The skin abrading head 18 includes an outer head portion 20 comprising an outer wall of cylindrical configuration. Outer head portion 20 has a circular rim 22 for placement in contact with the skin. The rim 22 is generally smooth and itself does not abrade the skin. Rather, as will be seen below, the outer head portion and rim thereof cooperate with a skin abrading brush comprising part of the skin abrading head.

Outer head portion 20 defines a head interior 24 and an opening 26 at the distal end of the skin abrading head in communication with the head interior.

The skin abrading head further includes a brush support in the form of an inner wall or partition 28. The brush support is disposed inwardly of and spaced from opening 26.

A skin abrading brush having a plurality of bristles is located in the head interior. More particularly, the skin abrading brush comprises a plurality of spaced brush segments 30, each of which has a plurality of bristles. The spaced brush segments 30 project outwardly from the brush support 28 in the direction of opening 26. The spaced brush segments have flattened outer distal brush segment ends 32 which in the illustrated embodiment are located at the plane of the rim. It is within the scope of the present invention to locate the flattened outer ends inwardly of the plane of the rim to some extent if desired.

A plurality of orifices 40 are defined by brush support 28, the orifices providing communication between air-flow passageway 14 and the head interior for creating a vacuum induced air flow within the head interior entraining skin portions removed due to abrasion of the skin by the skin abrading brush and delivering the skin portions to the air-flow passageway. In this embodiment of the invention the orifices 40 are located between the skin abrading brush and the outer head portion.

The spaced brush segments 30 are staggered to provide serpentine air-flow paths for the vacuum induced air flow within the head interior. It has been found that such an arrangement increases vacuum efficiency.

In operation, the rim 22 and the bristles of the brush segments are substantially simultaneously brought into engagement with the skin being treated.

While maintaining that engagement the hand-held member is utilized to move the rim and the bristles along the skin.

During such movement and while maintaining engagement, a vacuum is created in the air-flow passageway 14 and in the head interior 24 causing air flow from the ambient atmosphere under the rim 22, into and through the head interior past the bristles and into the air-flow passageway. This pulls the skin toward the rim and skin abrading brush. The skin abraded by the skin abrading brush are entrained in the air flow for removal and disposal.

The amount of vacuum in the head interior and bristle engagement with the skin can be controlled by tilting the rim relative to the skin. The vacuum produced in the head interior serves to maintain the skin in engagement with the rim and bristles. The stronger the vacuum, the tighter the engagement. The vacuum causes blood to move toward the abraded outer skin surface, promoting healing and formation of smooth, clear outermost skin layer.

The rim is substantially smooth and does not itself abrade the skin. The smooth beveling of the rim facilitates movement of the skin abrading head over the skin and facilitates user control and placement of the skin abrading head. Such an arrangement also has been found to essentially eliminate striping, the formation of red streaks on the skin that can otherwise occur. The outer head portion defines spaced air-flow recesses 44 located at the rim to prevent formation of a complete vacuum seal between the head and the skin even when the apparatus is disposed orthogonally relative to the skin. In this manner, blotchiness, irritation and other types of problems are unlikely to occur due to vacuum application.

Figure 5:
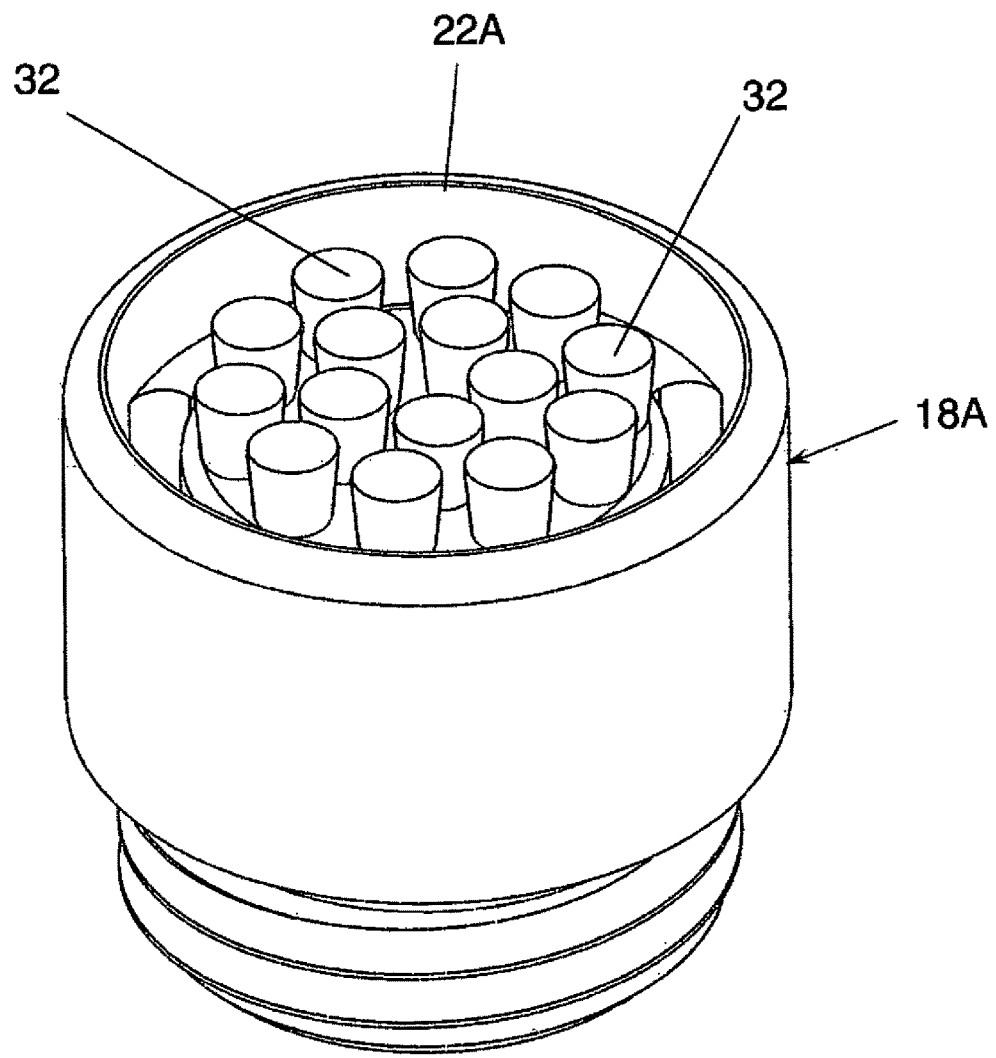
FIG. 5 is an enlarged view of an alternative embodiment of skin abrading head.

FIG. 5 shows an alternative skin abrading head 18A which, except for a couple of features, is identical to the skin abrading head 18 of FIGS. 1-4. In this embodiment, the distal brush segment ends 32 lie in a common plane spaced inwardly of the plane of rim 22A. Furthermore, no recesses equivalent to recesses 44 are formed in the rim, the rim being smoothly beveled and uniform about the entire periphery thereof.

Figure 6:
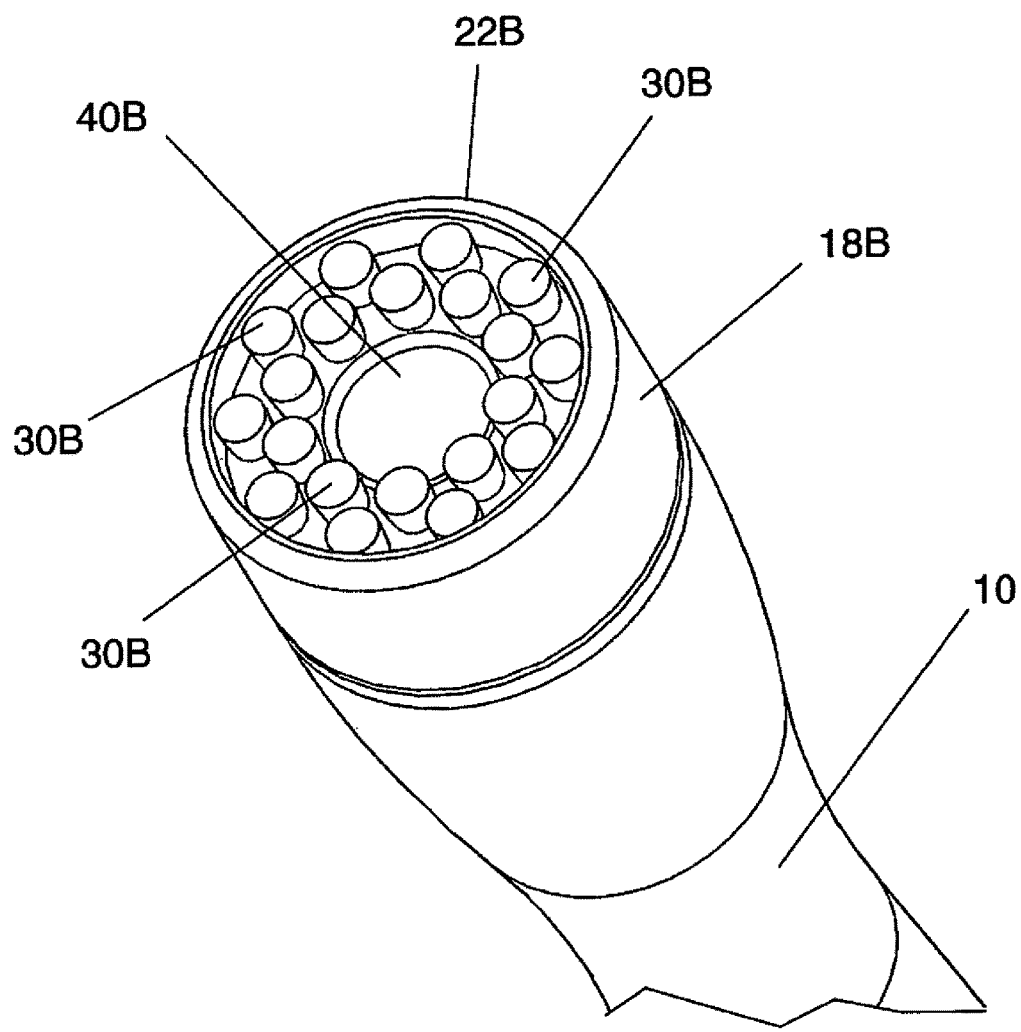
FIG. 6 is a view similar to FIG. 2, but illustrating a third embodiment of skin abrading head.

FIG. 6 shows a third embodiment of skin abrading head, the head identified by reference numeral 18B. In this embodiment a single orifice 40B provides communication between the air-flow passageway and the head interior. The orifice is centrally disposed within the skin abrading head. The brush segments 30B surround the orifice.

Figure 7:
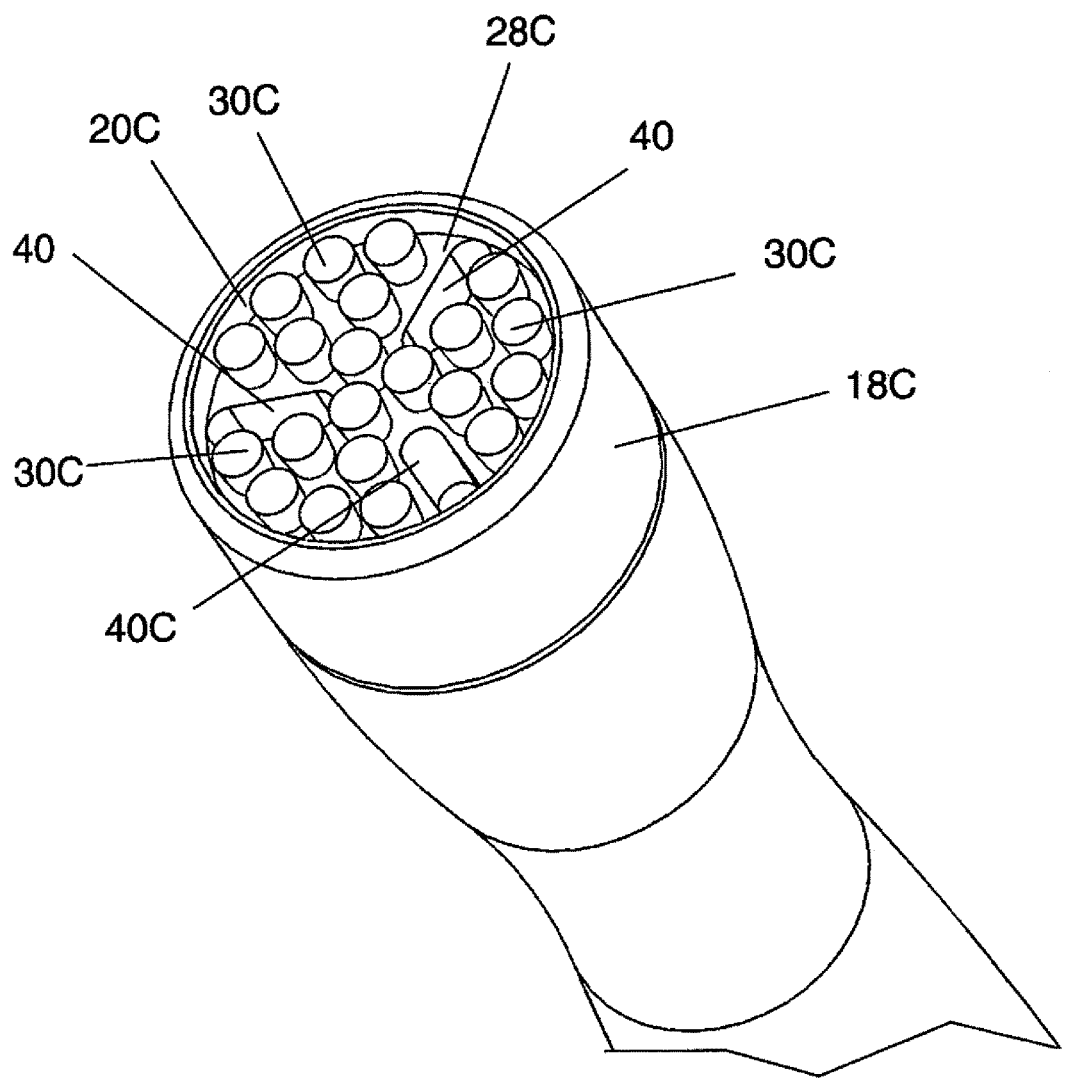
FIG. 7 is a view similar to FIGS. 2 and 6, but illustrating a fourth embodiment of skin abrading head constructed in accordance with the teachings of the present invention.

In the FIG. 7 embodiment, the skin abrading head 18C has a brush support 28C defining radially extending slots comprising the orifices 40C. The brush segments 30C are arrayed in clusters with the orifices 40C located between clusters and and the outer head portion 20C.

Figure 8:
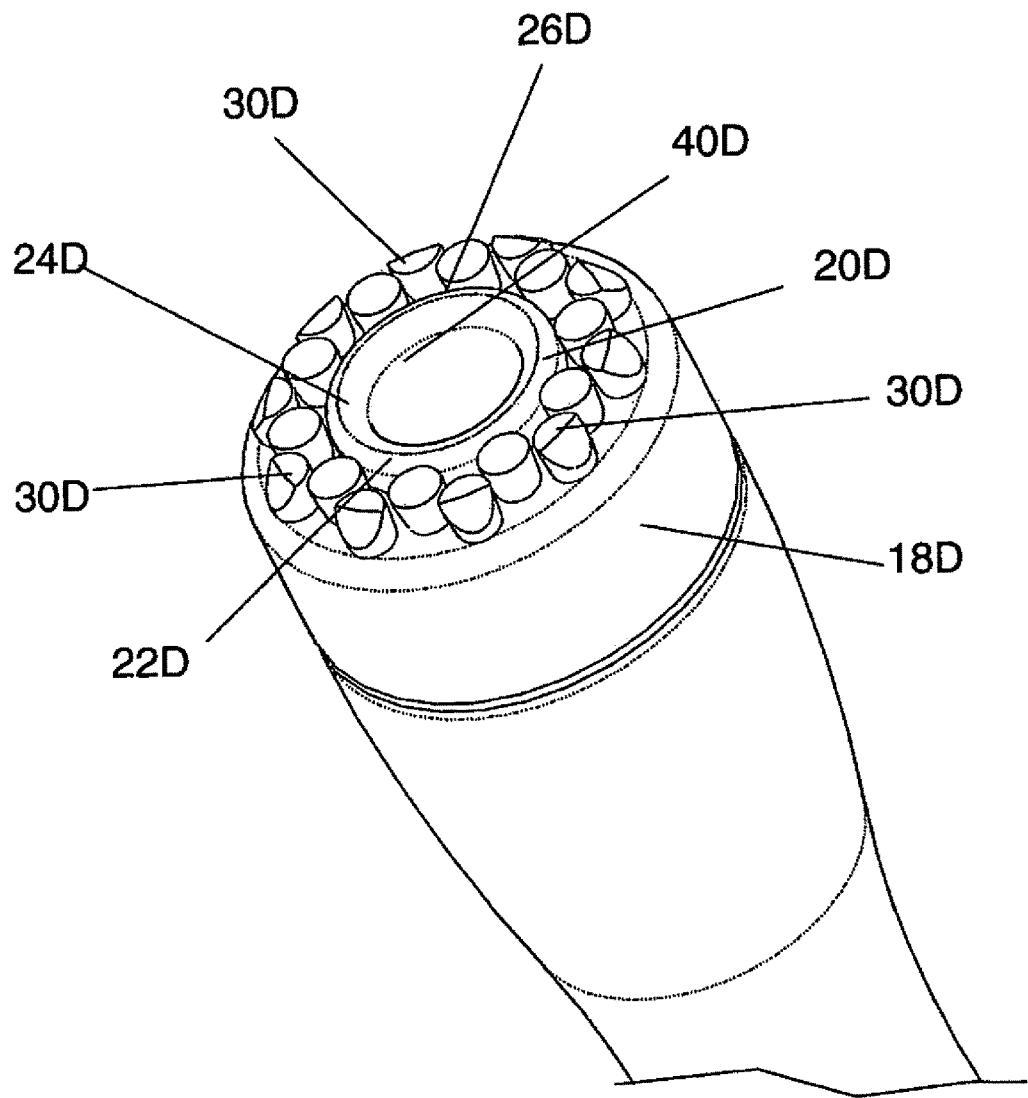
FIG. 8 is a view similar to FIGS. 2, 6 and 7, but illustrating yet another embodiment of skin abrading head constructed in accordance with the teachings of the present invention.

FIG. 8 shows another alternative embodiment of the invention. This embodiment is somewhat similar to the skin abrading head embodiment of FIG. 6. In the FIG. 8 head there is a single, centrally disposed orifice 40D. An inner wall or head portion 20D surrounds orifice 40D and extends upwardly therefrom to define head interior 24D and an opening 26D communicating with the head interior. The head portion 20D has an outer circular rim 22D. Brush segments 30D surround the inner head portion 20D. The outer brush segments are chambered to better conform to the skin surface and reduce likelihood of bristle separation when the head portion is tilted during use.

In the invention, the different skin abrading heads can be substituted for one another, depending upon the abrading and/or vacuum action desired. Not only can the head components have different configurations and sizes, different brush materials can be utilized.

The invention claimed is:

1. A method for abrading skin to remove outer portions thereof, said method comprising the steps of:

providing a hand-held member defining an air-flow passageway connected to a skin abrading head including a head portion having a rim and defining a head interior and a skin abrading brush having a plurality of bristles;

substantially simultaneously bring said rim and said bristles into engagement with the skin;

while maintaining said engagement utilizing said hand held member to move said rim and bristles along said skin;

during said movement and while maintaining said engagement, creating a vacuum in said air-flow passageway and in said head interior causing air flow from the ambient atmosphere through said head interior and past said bristles and into said air-flow passageway, wherein said air flow passes through air-flow recesses located at said rim;

selectively employing said vacuum to pull said skin in the direction of said rim and bristles;

abrading the skin with said bristles; and entraining in said air flow outer portions of said skin abraded by said skin abrading brush.

2. The method according to claim 1 wherein said skin abrading brush comprises a plurality of spaced brush segments substantially simultaneously brought into engagement with the skin, each brush segment having at least one bristle of the plurality of bristles.

3. The method according to claim 1 wherein air flowing from said head interior into said air-flow passageway flows through at least one orifice adjacent to said skin abrading brush.

4. The method according to claim 3 wherein said at least one orifice is located between at least some of said skin abrasion brush and said head portion.

5. The method according to claim 3 wherein said at least one orifice is substantially surrounded by said skin abrasion brush.

6. The method according to claim 3 including the step of flowing the air through serpentine flow paths defined by said skin abrasion brush on the way to said orifice.

7. The method according to claim 1 wherein said air flow is caused by creating a vacuum in said air-how passageway and in said head interior, the method including the step of employing said vacuum in said head interior to maintain engagement between said bristles and said skin.

* * * * *